(12) United States Patent
Haddach et al.

(10) Patent No.: US 6,348,466 B1
(45) Date of Patent: Feb. 19, 2002

(54) CRF RECEPTOR ANTAGONISTS AND METHODS RELATING THERETO

(75) Inventors: Mustapha Haddach; Zhiqiang Guo, both of San Diego, CA (US); James R. McCarthy, Zionsville, IN (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/439,841

(22) Filed: Nov. 12, 1999

Related U.S. Application Data

(63) Continuation-in-part of application No. 09/400,744, filed on Sep. 21, 1999, now abandoned, which is a continuation-in-part of application No. 09/190,958, filed on Nov. 12, 1998, now abandoned.

(51) Int. Cl.$^7$ ..................... A61K 31/495; A61K 31/50; C07D 471/12; C07D 487/12; A61P 25/00
(52) U.S. Cl. ...................................... 514/250; 544/346
(58) Field of Search ........................... 514/250; 544/346

(56) References Cited

U.S. PATENT DOCUMENTS

| | | | |
|---|---|---|---|
| 4,605,642 A | 8/1986 | Rivier et al. | 514/12 |
| 4,904,658 A | 2/1990 | Tseng et al. | 514/233.2 |
| 5,063,245 A | 11/1991 | Abreu et al. | 514/404 |
| 5,464,847 A | 11/1995 | Courtemanche et al. | 514/342 |
| 5,880,135 A | 3/1999 | Gully et al. | 514/307 |

FOREIGN PATENT DOCUMENTS

| | | |
|---|---|---|
| WO | WO 94/13643 | 6/1994 |
| WO | WO 94/13644 | 6/1994 |
| WO | WO 94/13661 | 6/1994 |
| WO | WO 94/13676 | 6/1994 |
| WO | WO 94/13677 | 6/1994 |
| WO | WO 95/10506 | 4/1995 |
| WO | WO 95/33750 | 12/1995 |
| WO | WO 95/34563 | 12/1995 |
| WO | WO 96/35689 | 11/1996 |
| WO | Wo 97/00868 | 1/1997 |
| WO | WO 97/35539 | 10/1997 |
| WO | WO 97/35580 | 10/1997 |
| WO | WO 97/35846 | 10/1997 |
| WO | WO 97/44038 | 11/1997 |
| WO | WO 98/03510 | 1/1998 |
| WO | WO 98/05661 | 2/1998 |
| WO | WO 98/08846 | 3/1998 |
| WO | WO 98/08847 | 3/1998 |
| WO | WO 98/11075 | 3/1998 |
| WO | WO 98/15543 | 4/1998 |
| WO | WO 98/21200 | 5/1998 |
| WO | WO 98/29413 | 7/1998 |

OTHER PUBLICATIONS

Rivier et al., "Synthetic Competitive Antagonists of Corticotropin–Releasing Factor: Effect on ACTH Secretion in the Rat," Science 224: 889–891, 1984.

De Souza et al., Heterogeneity of Corticotropin Releasing Factor Receptors: Multiple Targets for the Treatment of CNS and Inflammatory Disorders, Annual Reports in Medicinal Chemistry, vol. 30, pp. 21–30, 1995.*

McCarthy et al., Recent Progress in Corticotropin–Releasing Factor Receptor Agents, Annual Reports in Medicinal Chemistry, vol. 34, pp. 11–20, 1999.*

* cited by examiner

*Primary Examiner*—Brenda Coleman
(74) *Attorney, Agent, or Firm*—SEED Intellectual Property Law Group PLLC

(57) ABSTRACT

Compounds are disclosed which have utility in the treatment of a variety of disorders, including the treatment of disorders manifesting hypersecretion of CRF in a warm-blooded animals, including stroke. The compounds of this invention have the following structures:

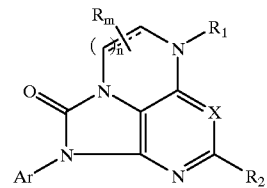

wherein n, m, R, $R_1$, $R_2$, X and Ar are as defined herein, including stereoisomes and pharmaceutically acceptable salts thereof.

18 Claims, No Drawings

CRF RECEPTOR ANTAGONISTS AND METHODS RELATING THERETO

CROSS REFERENCE TO RELATED APPLICATIONS

This application is a continuation-in-part of U.S. application Ser. No. 09/400,744, filed Sep. 21, 1999 now abandoned, which is a continuation-in-part of U.S. application Ser. No. 09/190,958, filed Nov. 12, 1998, now abandoned (which applications are incorporated herein by reference in their entirety).

TECHNICAL FIELD

This invention relates generally to CRF receptor antagonists, and to methods of treating disorders by administration of such antagonists to a warm-blooded animal in need thereof.

BACKGROUND OF THE INVENTION

The first corticotropin-releasing factor (CRF) was isolated from ovine hypothalmi and identified as a 41-amino acid peptide (Vale et al., Science 213:1394–1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394–1397, 1981). Briefly, CRF is believed to initiate its biological effects by binding to a plasma membrane receptor which has been found to be distributed throughout the brain (DeSouza et al., Science 224:1449–1451, 1984), pituitary (DeSouza et al., Methods Enzymol. 124:560, 1986; Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617, 1988). The CRF receptor is coupled to a GTP-binding protein (Perrin et al., Endocrinology 118:1171–1179, 1986) which mediates CRF-stimulated increase in intracellular production of cAMP (Bilezikjian, L. M., and W. W. Vale, Endocrinology 113:657–662, 1983). The receptor for CRF has now been cloned from rat (Perrin et al., Endo 133(6):3058–3061, 1993), and human brain (Chen et al., PNAS 90(19):8967–8971, 1993; Vita et al., FEBS 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555–2564, 1992; Sapolsky et al., Science 238:522–524, 1987; Tilders et al., Regul. Peptides 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 278:332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988). Furthermore, clinical data suggests that CRF may be hypersecreted in the brain in depression, anxiety-related disorders, and anorexia nervosa. (DeSouza, Ann. Reports in Med. Chem. 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyyrazoline derivatives (Abreu et al., U.S. Pat. No. 5,063,245) and substituted 2-aminothiazole derivatives (Courtemanche et al., Australian Patent No. AU-A-41399/93) have been reported as CRF receptor antagonists. These particular derivatives were found to be effective ine inhibiting the binding of CRF to its receptor in the 1–10 $\mu$M range and 0.1–10 $\mu$M range, respectively.

More recently, numerous small molecule CRR receptor antagonists have been proposed, including the compounds disclosed in the following patent documents: WO 94/13643, WO 94/13644, WO 94/13661, WO 94/13676, WO 94/13677, WO 95/10506, WO 95/33750, WO 96/35689, WO 97/00868, WO 97,35539, WO 97/35580, WO 97,35846, WO 97/44038, WO 98/03510, WO 98/05661, WO 98/08846, WO 98/08847, WO 98/11075, WO 98/15543, WO 98/21200 and WO 98/29413.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

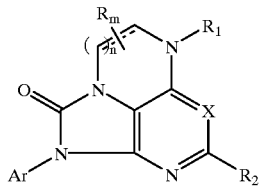

including stereoisomers and pharmaceutically acceptable salts thereof wherein m, n, X, R, $R_1$, $R_2$ and Ar are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention. preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists.

In a first embodiment, the CRF receptor antagonists of this invention have the following structure (I):

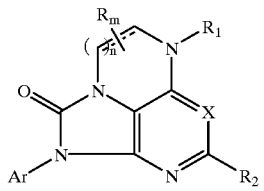

including stereoisomers and pharmaceutically acceptable salts thereof,
wherein:
  n is 1 or 2;
  m is 0, 1, 2 or 3;
  X is N or CR';
  R is an optional substituent which, at each occurrence, is independently $C_{1-6}$alkyl, $C_{3-6}$alkenyl $C_{1-6}$alkylidenyl or $C_{1-6}$alkylAr;
  R' is hydrogen, halogen or $C_{1-6}$alkyl;
  $R_1$ is —C(H)$_{0,1}$($R_3$)($R_4$);
  $R_2$ is hydrogen or $C_{1-6}$alkyl;
  $R_3$ is hydrogen, keto, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, or $C_{1-6}$alkyloxy$C_{1-6}$alkyl, and
  $R_4$ is hydrogen, $Ar^1$, $C_{1-6}$alkyl$Ar^1$, $OAr^1$, $C_{1-8}$alkyl, $C_{1-6}$alkyloxy, $C_{3-6}$cycloalkyl, mono- or di($C_{3-6}$cycloalkyl)methyl, $C_{3-6}$alkenyl, $C_{3-6}$alkynyl, $C_{1-6}$alkyloxy$C_{1-6}$alkyl, $C_{1-6}$alkoxy$Ar^1$, hydroxy$C_{1-6}$alkyl, thienyl$C_{1-6}$alkyl, furanyl$C_{1-6}$alkyl, $C_{1-6}$alkylthio$C_{1-6}$alkyl, morpholinyl, mono- or di($C_{1-6}$alkyl)amino$C_{1-6}$alkyl, amino, ($C_{1-6}$alkyl)amino, di($C_{1-6}$alkyl)amino, ($C_{1-6}$alkyl$Ar^1$)amino, ($C_{1-6}$alkyl)($Ar^1$)amino, $C_{1-6}$alkylcarbonyl$C_{1-6}$alkyl, $C_{1-6}$alkylcarbonyloxy$C_{1-6}$alkyl, sulfonyl($C_{1-8}$alkyl), C(=O)$C_{1-6}$alkyl, $C_{1-8}$alkyl substituted with phthalimide, $Ar^1$, $OAr^1$, $NHAr^1$, C(=O)$Ar^1$, C(=O)$NHAr^1$ or —C(=O)$NH_2$, or a radical of the formula —($C_{1-6}$alkanediyl)-Y—(CO)$_{0,1}$—$Ar^1$ where Y is O, NH or a direct bond, or
  $R_3$ and $R_4$ taken together with the carbon atom to which they are attached form a $C_{5-8}$cycloalkyl, a $C_{5-8}$cycloalkenyl, a $C_{3-12}$heterocycle, phenyl, naphthyl, or a $C_{5-8}$cycloalkyl fused to $Ar^1$, each of which being optionally substituted with one or more substituents independently selected from $C_{1-6}$alkyl;
  Ar is phenyl, naphthyl or an aromatic $C_{3-12}$heterocycle, each being optionally substituted with 1, 2 or 3 substituents independently selected from halo, $C_{1-6}$alkyl, trifluoromethyl, O(trifluoromethyl), hydroxy, cyano, $C_{1-6}$alkyloxy, phenoxy, benzoxy, $C_{1-6}$alkylthio, nitro, amino, mono- or di($C_{1-6}$alkyl)amino, ($C_{1-6}$alkyl)($C_{1-6}$alkanoyl)amino, or piperidinyl, or wherein two substituents taken together are a $C_{1-6}$alkylidinyl or a $C_{1-6}$alkylidenyl having one, two or three carbon atoms replaced with a heteroatom individually selected from oxygen, nitrogen or and sulfur; and
  $Ar^1$ is phenyl, naphthyl or an aromatic $C_{3-12}$heterocycle, each of which being optionally substituted with 1, 2 or 3 substituents independently selected from halo, $C_{1-6}$alkyl, $C_{1-6}$alkyloxy, di($C_{1-6}$alkyl)amino, di($C_{1-6}$alkyl)amino$C_{1-6}$alkyl, trifluoromethyl sulfanyl($C_{1-6}$alkyl), and $C_{1-6}$alkyl substituted with morpholinyl.

In the context of this invention, the preceding terms have the meanings set forth below.

"Keto" represents =O.

"$C_{1-6}$alkyl" or "$C_{1-8}$alkyl" represents a straight chain or branched alkyl having from 1 to 6 carbon atoms or 1 to 8 carbon atoms, respectively, such as methyl, ethyl, n-propyl, isopropyl, n-butyl, tert-butyl, n-pentyl, and the like.

"$C_{1-6}$alkyloxy" represents the group —O($C_{1-6}$alkyl), such as methoxy, ethoxy, and the like.

"$C_{1-6}$alkylthio" represents the group —S($C_{1-6}$alkyl), such as —SCH$_3$, —SCH$_2$CH$_3$, and the like.

"$C_{3-6}$cycloalkyl" represents a cyclic alkyl having from 3 to 6 carbon atoms, including cyclopropyl, cyclopentyl, cyclopentyl, and cyclohexyl.

"$C_{5-8}$cycloalkyl" represents a cyclic alkyl having from 5 to 8 carbon atoms, such as cyclopentyl, cyclohexyl, and the like.

"$C_{5-8}$cycloalkenyl" represents a cyclic alkyl having from 5 to 8 carbon atoms an at least one double bond.

"$C_{3-6}$alkenyl" represents an unsaturated straight chain or branched alkyl having from 3 to 6 carbon atoms, and having at least one double bond, such as propylenyl, 1-butenyl, 2-butenyl, 2-methylpropenyl, and the like.

"$C_{3-6}$alkynyl" represents an unsaturated straight chain or branched alkyl having from 3 to 6 carbon atoms, and having at least one triple bond, such as propylynyl, 1-butynyl, 2-butynyl, 2-methylpropynyl, and the like.

"HydroxyC$_{1-6}$alkyl" represents a C$_{1-6}$alkyl substituted with at least one hydroxyl group, such as —CH$_2$OH, —CH(OH)CH$_3$, and the like.

"Mono- or di(C$_{3-6}$cycloalkyl)methyl" represents a methyl group substituted with one or two C$_{3-6}$cycloalkyl groups, such as cyclopropylmethyl, dicyclopropylmethyl, and the like.

"C$_{1-6}$alkylcarbonylC$_{1-6}$alkyl" represents a C$_{1-6}$alkyl substituted with a —COC$_{1-6}$alkyl group.

"C$_{1-6}$alkylcarbonyloxyC$_{1-6}$alkyl" represents a C$_{1-6}$alkyl substituted with a —COOC$_{1-6}$alkyl group.

"C$_{1-6}$alkyloxyC$_{1-6}$alkyl" represents a C$_{1-6}$alkyl substituted with a —OC$_{1-6}$alkyl group.

"C$_{1-6}$alkylthioC$_{1-6}$alkyl" represents a C$_{1-6}$alkyl substituted with a —SC$_{1-6}$alkyl group.

"Sulfanyl(C$_{1-6}$alkyl)" means —SO$_2$(C$_{1-6}$alkyl), such as —SO$_2$ methyl and the like.

"Mono- or di(C$_{1-6}$alkyl)amino represents an amino substituted with one C$_{1-6}$alkyl or with two C$_{1-6}$alkyls, respectively.

"(C$_{1-6}$alkyl)(C$_{1-6}$alkanoyl)amino" represents an amino substituted with a C$_{1-6}$alkyl and a C$_{1-6}$alkanoyl (i.e., C(=O)(C$_{1-6}$alkyl).

"Mono- or di(C$_{1-6}$alkyl)aminoC$_{1-6}$alkyl" represents a C$_{1-6}$alkyl substituted with a mono- or di(C$_{1-6}$alkyl) amino.

"C$_{1-6}$alkylidenyl" represents a divalent C$_{1-6}$alkyl radical, such as methylene (—CH$_2$—), ethylene (—CH$_2$CH$_2$—), and the like.

"C$_{1-6}$alkylidenyl having one, two or three carbon atoms replaced with a heteroatom individually selected from oxygen, nitrogen or and sulfur" means a C$_{1-6}$alkylidenyl wherein one, two or three methylenyl groups (i.e., "CH$_2$") is replaced with O, N or S, such as —OCH$_2$O—, —OCH$_2$CH$_2$O—, and the like.

"C$_{3-12}$heterocycle" represents a ring made up of more than one kind of atom, and which contains 3 to 12 carbon atoms, such as pyridinyl, pyrimidinyl, furanyl, thienyl, imidazolyl, thiazolyl, pyrazolyl, pyridazinyl, pyrazinyl, triazinyl (such as 1,3,5), pyrrolyl, thiopenyl, oxazolyl, isoxazoly, pyrrolinyl, pyrrolidinyl, piperidinyl, and the like, as well as heterocyclic rings fused to phenyl to form a bicyclic ring, such as pyrolidinophenyl and the like.

"Halo" means fluoro, chloro, bromo or iodo.

As used in the context of this invention,

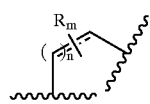

represents —CH$_2$CH$_2$— or —CH=CH— optionally substituted with 1 or 2 R substituents (i.e., when n=1 and m=0, 1 or 2), or —CH$_2$CH$_2$CH$_2$— optionally substituted with 1, 2 or 3 R substituents (i.e., when n=2 and m=0, 1, 2 or 3). Accordingly, representative compounds of this invention include (but are not limited to) compounds having the following structures (I-1), (I-2), (I-3), (I-4), (I-5) and (I-6):

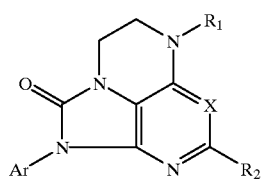
(I-1)

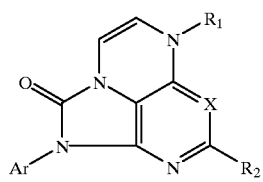
(I-2)

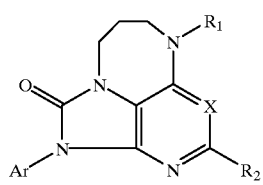
(I-3)

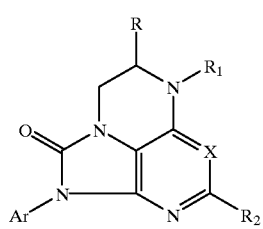
(I-4)

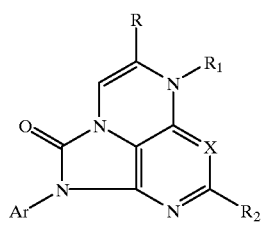
(I-5)

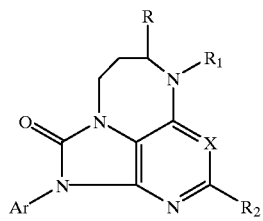
(I-6)

More specifically, and depending upon the choice of the X moiety, representative CRF receptor antagonists of this invention include compounds having the following structures (Ia) and (Ib), respectively:

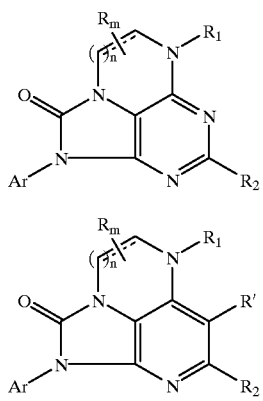

(Ia)

(Ib)

In one preferred embodiment, the CRF receptor antagonists of this invention have structure (Ia). In another preferred embodiment, the CRF receptor antagonists of this invention have structure (Ib), wherein R' is hydrogen. Such compounds are represented by the following structures (I-1a), (I-1b), (I-4a) and (I-4b):

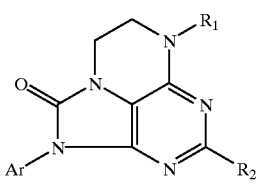

(I-1a)

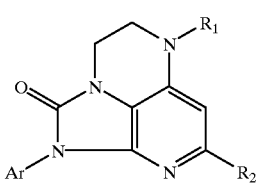

(I-1b)

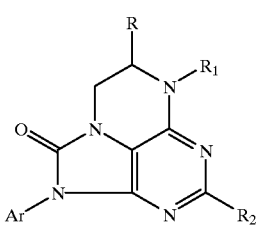

(I-4a)

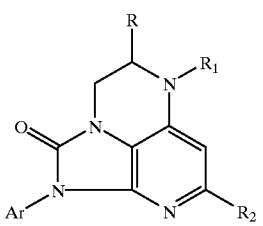

(I-4b)

As noted above, $R_1$ is —C(H)$_{0,1}$(R$_3$)(R$_4$) which represents —CH(R$_3$)(R$_4$) and —C(R$_3$)(R$_4$). Representative embodiments in this regard include the following R$_1$ moieties:

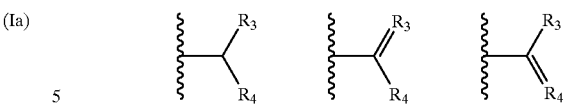

Similarly, when $R_3$ is keto, representative $R_1$ moieties include the following:

Representative $R_1$ moieties in this regard include —C(=O)R$_4$, —C(=O)OR$_4$, —C(=O)NH$_2$, —C(=O)NH(C$_{1-6}$alkyl) and —C(=O)N(C$_{1-6}$alkyl)(C$_{1-6}$alkyl).

In the embodiment where the $R_3$ and $R_4$ groups of $R_1$ taken together form a C$_{3-8}$cycloalkyl, the resulting $R_1$ group has the structure:

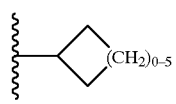

Representative C$_{3-8}$cycloalkyls include cyclopropyl, cyclopentyl and cyclohexyl. Furthermore, when the C$_{3-8}$cycloalkyl is a C$_{5-7}$cycloalkyl, optionally substituted with one or more C$_{1-6}$alkyl groups, a representative $R_1$ moiety has the following structure:

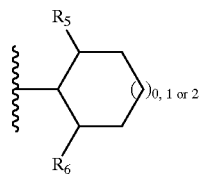

wherein $R_5$ and $R_6$ are the same or different and independently selected from a C$_{1-6}$alkyl, such as methyl or ethyl.

Similarly, in the embodiment where the $R_3$ and $R_4$ groups of $R_1$ taken together form a C$_{5-8}$cycloalkyl fused to Ar, the resulting $R_1$ group has the structure:

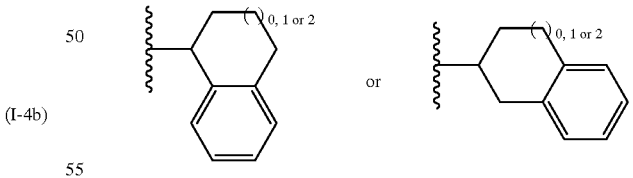

including optionally substituted analogs thereof as defined above.

In more specific embodiments of this invention, representative Ar groups of this invention include 2,4,6-trimethylphenyl, 2-chloro-4-methylphenyl, 2-chloro-4-methoxyphenyl, 2-bromo-4-methylphenyl, 2-methyl-4-chlorophenyl, 2-methyl-4-bromophenyl, 2-bromo-4-isopropylphenyl, 2,4-dichlorophenyl, 2,6-dimethyl-4-bromophenyl, 4-chlorophenyl, 2,4-dimethoxyphenyl, 2,4-dimethylphenyl, 2-methoxyphenyl, 3-methoxyphenyl, 2-methyl-4-methoxyphenyl, 3,4-dimethoxyphenyl, 3,5- dimethoxyphenyhl, 4-trifluoromethylphenyl, 4-methoxyphenyl, 2,4,6-trifluorophenyl, 2-methyl-4-N(ethyl)$_2$phenyl, 2-bromo-4-(OCF$_3$)phenyl, 4-dimethylamino-2-methyl-3-pyrdinyl, 4-dimethylamino-6-methyl-2-pyridinyl, 4-dimethylamino-3-pyridinyl. 4-N(CH$_3$)(COCH$_3$)-phenyl, 3,4-methylenedioxyphenyl and 3,4-ethylenedioxyphenyl.

Representative optional R groups of this invention include methyl, ethyl, n-propyl, iso-propyl, iso-butyl, =CH$_2$ and =CHCH$_3$.

Representative R' groups are hydrogen, fluoro, chloro, bromo, methyl and ethyl, and preferably hydrogen.

Representative R$_1$ groups include methyl, ethyl, n-propyl, iso-propyl, n-butyl, iso-butyl, tert-butyl, n-pentyl, iso-pentyl, neo-pentyl, —CH(ethyl)$_2$, —CH(n-propyl)$_2$, —CH(n-butyl)$_2$, —CH$_2$CH$_2$OCH$_3$, —CH(methyl)(CH$_2$OCH$_3$), —CH(ethyl)(CH$_2$OCH$_3$), —CH(n-propyl)(CH$_2$OCH$_3$), —CH(n-butyl)(CH$_2$OCH$_3$), —CH(tert-butyl)(CH$_2$OCH$_3$), —CH(CH$_2$OCH$_3$)$_2$, —CH(benzyl)(CH$_2$OCH$_3$), —CH(4-chlorobenzyl)(CH$_2$OCH$_3$), —CH(CH$_2$OCH$_3$)(CH$_2$CH$_2$SCH$_3$), —CH(ethyl)(CH$_2$Obenzyl), —CHC≡CH, —CH(methyl)(ethyl), —CH(methyl)(n-propyl), —CH(methyl)(n-butyl), —CH(methyl)(n-pentyl), —CH(methyl)(CH$_2$CH$_2$CH$_2$CH(CH$_3$)$_2$), —CH(ethyl)(n-propyl), —CH(ethyl)(n-butyl), —CH(ethyl)(n-pentyl), —CH(n-propyl)(n-butyl), —CH(n-propyl)(n-pentyl), cyclopropyl, cyclobutyl, cyclohexyl, 2-methylcyclohexyl, 3-methylcyclohexyl, 1,2,3,4-tetrahydronaphthyl (1 and 2), benzyl, 2-chlorobenzyl, —CH(methyl)(benzyl), —CH(ethyl)(benzyl), —CH(n-propyl)(benzyl), —CH(n-butyl)(benzyl), —CH$_2$(cyclopropyl), —CH$_2$(cyclobutyl), —CH$_2$CH(methyl)CH$_2$CH$_3$, —CH$_2$CH(ethyl)CH$_2$CH$_3$, —CH$_2$C(methyl)$_3$, —CH$_2$C≡CH, —CH$_2$C(=O)ethyl, —C(=O)cyclopropyl, —C(=O)NHbenzyl, —C(=O)methyl, —C(=O)benzyl, —C(=O)phenyl, —C(=O)ethyl, —C(=O)CH$_2$C(=O)Oethyl, —C(=O)CH(phenyl)ethyl, C(=O)pyridyl, —C(=O)(4-N,N-dimethylamino)phenyl, —C(=O)CH$_2$Omethyl, —C(=O)CH(ethyl)$_2$, —C(=O)n-butyl, —C(=O)CH$_2$CH$_2$(methyl)$_2$, —C(=O)n-propyl, —C(=O)CH$_2$CH$_2$phenyl, —CH$_2$pyridyl, —CH$_2$CH$_2$NHphenyl, —CH$_2$CH$_2$C(=O)Oethyl, —CH$_2$CH$_2$CH$_2$phenyl, —CH$_2$CH$_2$—N-phthalimide, —CH$_2$CH$_2$CH$_2$C(=O)Oethyl, —CH$_2$CH$_2$Oethyl, —CH$_2$CH(methyl)$_2$, —CH$_2$C(=O)Oethyl, —CH$_2$C(=O)pyrrohdinophenyl, —CH$_2$CH$_2$Ophenyl, —CH$_2$CH$_2$CH$_2$CH$_2$—N-phthalimide, —CH$_2$C(=O)Ot-butyl, —CH$_2$CH$_2$CH(methyl)$_2$, —CH$_2$C(=O)NH$_2$, —CH$_2$-4-(SO$_2$CH$_3$)phenyl, —CH$_2$CH$_2$pyrolyl and benzyl.

Representative R$_2$ groups include methyl, ethyl and hydrogen, and preferably methyl.

The compounds of the present invention may be prepared by known organic synthesis techniques, including the methods described in more detail in the Examples, and may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

More specifically, the compounds of the structure (I) may be made according to the procedures set forth in Examples 1 and 2, as well as by the following general Reaction Scheme:

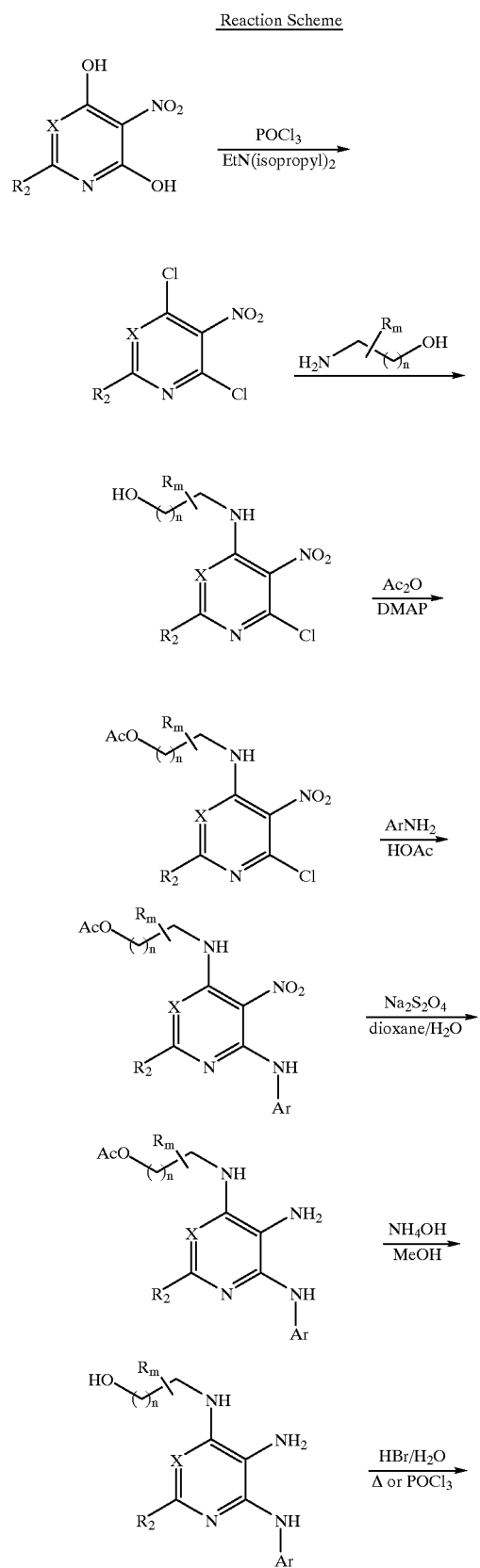

-continued

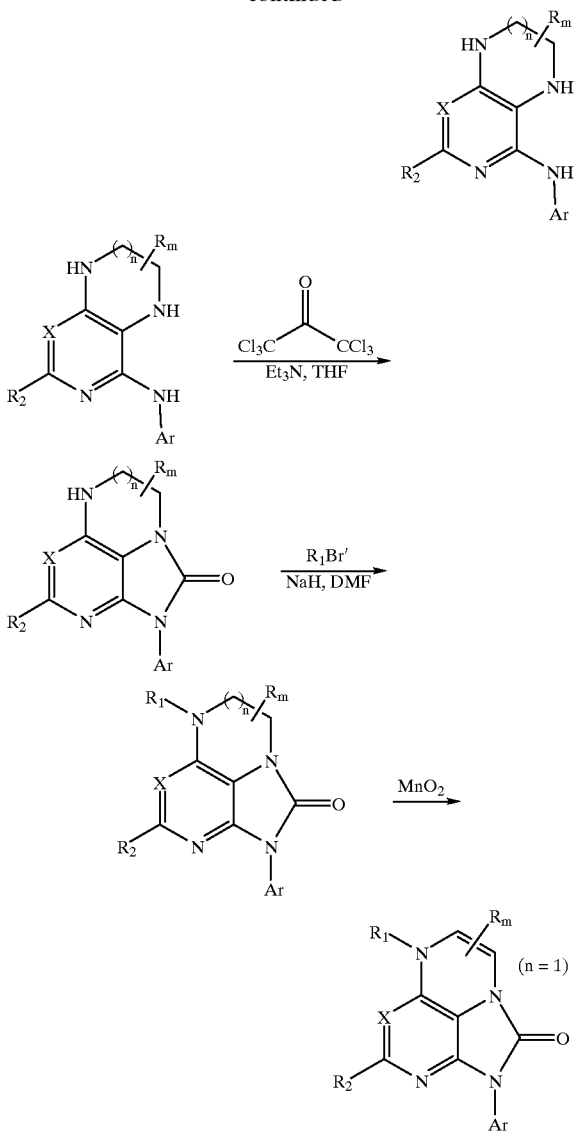

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}$I] tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM). As set forth in greater detail below, representative compounds of this invention were assayed by the method of Example 4. Preferred compounds having a $K_i$ of less than 1 μM are compounds numbers (I-1) through (I-25) and (I-29) through (I-33). More preferred compounds having a $K_i$ of less than 250 nM are compound numbers (I-1) through (I-14), (I-16) through (I-25) and (I-29) through (I-32).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the palient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences,* Gennaro, Ed., Mack Publishing Co., Easton, Pa. 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1–2.

Example 3 discloses representative compounds of this invention. Example 4 presents a method for determining the receptor binding activity ($K_i$), and Example 5 discloses an assay for screening compounds of this invention for CRF-stimulated adenylate cyclase activity.

Example 1

Synthesis of Representative Compounds of Structure (Ia)

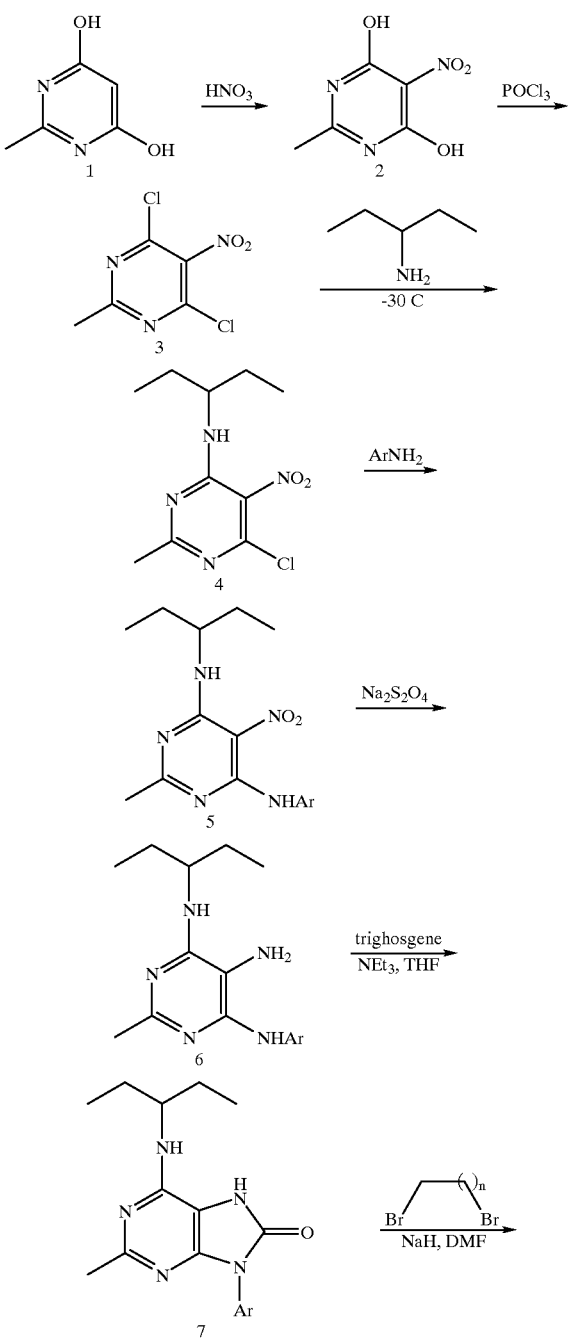

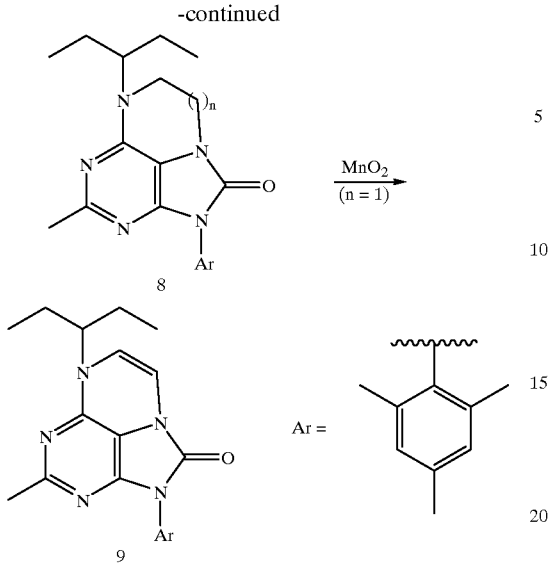

Compound (4)

A solution of 4,6-dichloro-2-methyl-5-nitropyrimidine (3; *J. Chem. Soc.* 1954, 3836) (2.23 g, 11 mmol) in EtOH (30 mL) at −30° C. was treated with 1-ethylpropylamine (870 mg, 10 mmol) in EtOH (8 mL) and the reaction mixture was stirred at −30 ° C. for 1 hour and then warmed to ambient temperature. Volatiles were evaporated and the residue was partitioned between water and EtOAc. The organic layer was dried (sodium sulfate), evaporated, purified by flash chromatography (silica) to give compound (4).

Compound (5)

A solution of compound (4) (2.07 g, 8 mmol) in acetonitrile (15 mL) was treated with 2,4,6-trimethylaniline (1.35 g, 10 mmol) at ambient temperature, then triethylamine (1.52 g, 15 mmol) was introduced. The reaction mixture was stirred at ambient temperature for 2 hours. Volatiles were evaporated and the residue was is partitioned between brine and EtOAc. The organic layer was dried (sodium sulfate), evaporated, purified by flash chromatography (silica) to give compound (5).

Compound (6)

Compound (5) (2.14 g, 6 mmol) was dissolved in 1:1 dioxane/water (20 mL), and treated with concentrated aqueous ammonia hydroxide (5 mL). Sodium hydrosulfite (3.12 g, 18 mmol) was added in small batches over one hour and the solution was stirred at ambient temperature for 8 hours. The reaction mixture was partitioned between brine and EtOAc. The organic layer was dried (sodium sulfate), evaporated, purified by flash chromatography (silica) to give compound (6).

Compound (7)

A mixture of compound (6) (654 mg, 2 mmol) and triethylamine (500 mg) in dry THF (10 mL) was treated with triphosgene (217 mg, 0.73 mmol), and the reaction mixture was stirred at ambient temperature for 1 hour. Precipitates were filtered and the filtrate was evaporated, and the residue was partitioned between brine and EtOAc. The organic layer was dried (sodium sulfate), evaporated, purified by flash chromatography (silica) to give compound (7).

Compound (8)

Compound (7) (353 mg, 1 mmol) in dry DMF (5 mL) was treated with NaH (120 mg, 3 mmol, 60% in oil) at ambient temperature. Then 1,2-dibromoethane (654 mg, 3 mmol) was added to the reaction mixture and stirred for 10 hours. The reaction mixture was partitioned between water and EtOAc. The organic layer was dried (sodium sulfate), evaporated, purified by flash chromatography (silica) to give compound (8). LC-MS 380 (MH+).

Compound (9)

A solution of compound (8) (38 mg, 0.1 mmol) in toluene (2 ml) was treated with activated manganese dioxide catalyst (100 mg) at reflux for 16 hours. The catalyst was removed by filtration through a Celite pad and the filtrate was evaporated to dryness and purified by Prepative TLC (silica gel) with ethyl acetate hexane (1:1) to provide compound (9).

Example 2

Synthesis of Representative Compounds of Structure (Ib)

Compounds of structure (Ib) may be made by the same synthetic route as disclosed above in Example 1, but employing the corresponding pyridine to compound (1) rather than the pyrimidine. For example, representative compounds of this invention may be made by the following reaction scheme:

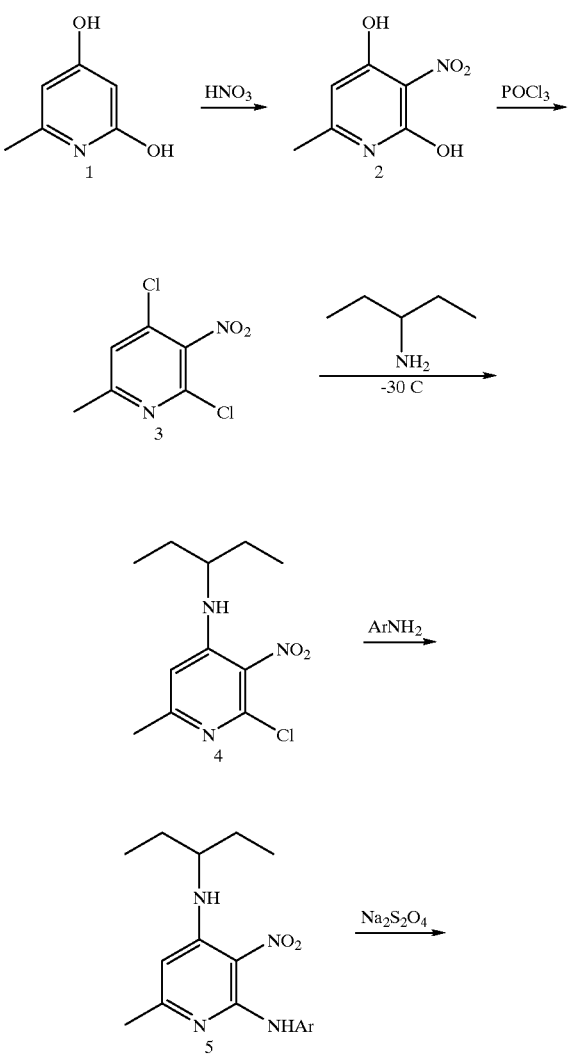

-continued

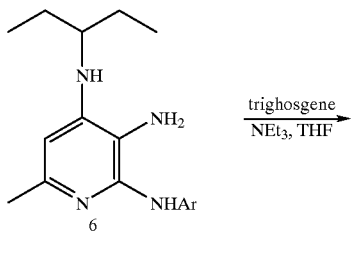

trighosgene
―――――――→
NEt₃, THF

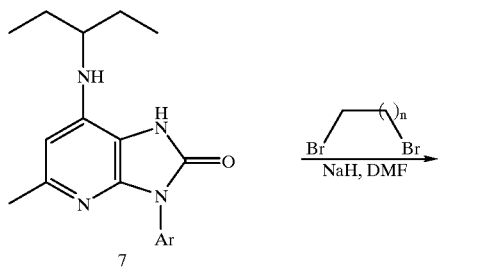

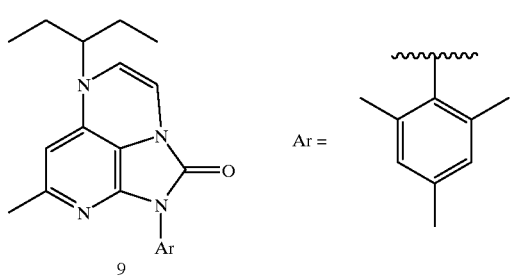

Ar =

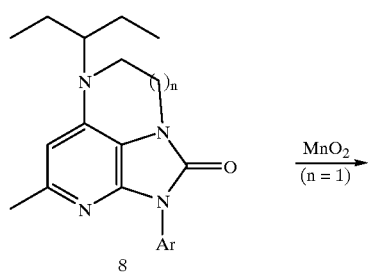

Br(CH₂)ₙBr
―――――――→
NaH, DMF

MnO₂
―――→
(n = 1)

Example 3

Synthesis of Representative Compounds

Further representative compounds of this invention were made by general Reaction Scheme disclosed above and/or by the procedures of Examples 1 and 2, and are presented in the following Table.

TABLE

Representative Compounds

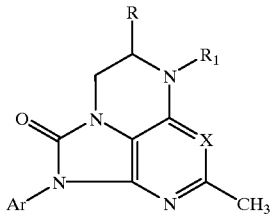

| Cpd | R | X | R₁ | Ar |
|---|---|---|---|---|
| (I-1) | H | N | —CH(CH₂CH₂CH₃)₂ | 2,4,6-trimethylphenyl |
| (I-2) | H | CH | —CH(CH₂CH₂CH₃)₂ | 2-chloro-4-methylphenyl |
| (I-3) | H | CH | —CH(CH₂CH₂CH₃)₂ | 2-bromo-4-isopropylphenyl |
| (I-4) | H | CH | —CH(CH₂CH₂CH₃)₂ | 2,4-dichlorophenyl |
| (I-5) | H | CH | —CH(CH₂CH₂CH₃)₂ | 2,6-dimethyl-4-bromophenyl |
| (I-6) | H | CH | —CH(CH₂CH₂CH₃)₂ | 2-methyl-4-chlorophenyl |
| (I-7) | H | CH | —CH(CH₂CH₂CH₃)₂ | 2-bromo-4-methylphenyl |
| (I-8) | H | CH | —CH(CH₂CH₂CH₃)₂ | 4-chlorophenyl |
| (I-9) | H | CH | —CH(CH₂CH₂CH₃)₂ | 2,4-dimethoxyphenyl |
| (I-10) | H | CH | —CH(CH₂CH₂CH₃)₂ | 2-methoxyphenyl |
| (I-11) | H | CH | —CH(CH₂CH₂CH₃)₂ | 3,4-dimethoxyphenyl |

TABLE-continued

Representative Compounds

| | | | | |
|---|---|---|---|---|
| (I-12) | H | CH | —CH(CH$_2$CH$_2$CH$_3$)$_2$ | 4-trifluoromethylphenyl |
| (I-13) | H | CH | —CH(CH$_2$CH$_2$CH$_3$)$_2$ | 4-methoxyphenyl |
| (I-14) | H | CH | —CH(CH$_2$CH$_2$CH$_3$)$_2$ | 2,4,6-trifluorophenyl |
| (I-15) | H | CH | —CH(CH$_2$CH$_2$CH$_3$)$_2$ | 2-methyl-4-(diethylamine)phenyl |
| (I-16) | H | CH | —CH(CH$_2$CH$_2$CH$_3$)$_2$ | 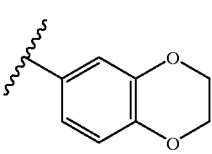 |
| (I-17) | H | CH | —CH(CH$_2$CH$_2$CH$_3$)$_2$ | 2-bromo-4-(OCF$_3$)phenyl |
| (I-18) | H | CH | —CH(CH$_2$CH$_2$CH$_3$)$_2$ | 3-methoxyphenyl |
| (I-19) | H | CH | —CH(CH$_2$CH$_2$CH$_3$)$_2$ | 2,4-dimethylphenyl |
| (I-20) | H | CH | —CH(CH$_2$CH$_2$CH$_3$)$_2$ | 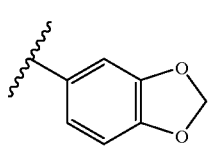 |
| (I-21) | H | CH | —CH(CH$_2$CH$_3$)((CH$_2$)$_3$CH$_3$) | 2-methyl-4-chlorophenyl |
| (I-22) | H | CH | —CH(CH$_2$CH$_3$)$_2$ | 2-methyl-4-chlorophenyl |
| (I-23) | H | CH | —CH(CH$_2$CH$_3$)((CH$_2$)$_2$CH$_3$) | 2-methyl-4-chlorophenyl |
| (I-24) | H | CH | —CH(CH$_2$CH$_3$)((CH$_2$)$_4$CH$_3$) | 2-methyl-4-chlorophenyl |
| (I-25) | H | CH | —CH((CH$_2$)$_2$CH$_3$)((CH$_2$)$_3$CH$_3$) | 2-methyl-4-chlorophenyl |
| (I-26) | H | CH | —CH(CH$_2$CH$_2$CH$_3$)$_2$ | 3,5-dimethoxyphenyl |
| (I-27) | H | CH | —CH(CH$_2$CH$_2$CH$_3$)$_2$ | 3-(5-methylisoxazolyl) |
| (I-28) | H | CH | —CH(CH$_2$CH$_2$CH$_3$)$_2$ | 4-phenoxyphenyl |
| (I-29) | H | CH | —CH(CH$_2$CH$_2$CH$_3$)$_2$ | 4-methoxy-3-pyridinyl |
| (I-30) | H | CH | —CH(CH$_2$CH$_2$CH$_3$)$_2$ | 4-dimethylamine-3-pyridinyl |
| (I-31) | ethyl(S) | CH | —CH$_2$CH$_2$OCH$_3$ | 4-methoxyphenyl |
| (I-32) | ethyl(S) | CH | —CH$_2$CH$_2$OH | 4-methoxyphenyl |
| (I-33) | H | CH | —CH(CH$_2$CH$_2$CH$_3$)$_2$ | 4-(N-methyl-N-acetyl)phenyl |
| (I-34) | ethyl(S) | CH | —CH$_2$CH$_2$N(CH$_2$CH$_3$)$_2$ | 4-methoxyphenyl |
| (I-35) | H | CH | —CH(CH$_2$CH$_2$CH$_3$)$_2$ | 4-(COOMe)phenyl |
| (I-36) | H | CH | —CH(CH$_2$CH$_2$CH$_3$)$_2$ | 4-chloro-3-pyridinyl |
| (I-37) | H | CH | —CH(CH$_2$CH$_2$CH$_3$)$_2$ | 4-(COMe)phenyl |
| (I-38) | H | CH | —CH(CH$_2$CH$_2$CH$_3$)$_2$ | 4-(CH(OH)(CH$_3$)$_2$)phenyl |
| (I-39) | ethyl(S) | CH | C(O)CH$_3$ | 4-methoxyphenyl |
| (I-40) | ethyl(S) | CH | C(O)CH$_2$Ph | 4-methoxyphenyl |
| (I-41) | ethyl(S) | CH | C(O)Ph | 4-methoxyphenyl |
| (I-42) | ethyl(S) | CH | C(O)CH$_2$CH$_3$ | 4-methoxyphenyl |
| (I-43) | ethyl(S) | CH | C(O)CH$_2$CO$_2$CH$_2$CH$_3$ | 4-methoxyphenyl |
| (I-44) | ethyl(S) | CH | C(O)Cyclopropyl | 4-methoxyphenyl |
| (I-45) | ethyl(S) | CH | C(O)CH(Ph)CH$_2$CH$_3$ | 4-methoxyphenyl |
| (I-46) | ethyl(S) | CH | C(O)4-Pyridyl | 4-methoxyphenyl |
| (I-47) | ethyl(S) | CH | C(O)4-(N,N-Dimethylamino)phenyl | 4-methoxyphenyl |
| (I-48) | ethyl(S) | CH | C(O)CH$_2$OCH$_3$ | 4-methoxyphenyl |
| (I-49) | ethyl(S) | CH | C(O)3-Pyridyl | 4-methoxyphenyl |
| (I-50) | ethyl(S) | CH | C(O)CH(CH$_2$CH$_3$)CH$_2$CH$_3$ | 4-methoxyphenyl |
| (I-51) | ethyl(S) | CH | C(O)CH$_2$CH$_2$CH$_2$CH$_3$ | 4-methoxyphenyl |
| (I-52) | ethyl(S) | CH | C(O)CH$_2$CH(CH$_3$)$_2$ | 4-methoxyphenyl |
| (I-53) | ethyl(S) | CH | C(O)CH$_2$CH$_2$CH$_3$ | 4-methoxyphenyl |
| (I-54) | ethyl(S) | CH | C(O)CH$_2$CH$_2$Ph | 4-methoxyphenyl |
| (I-55) | ethyl(S) | CH | CH$_2$-3-Pyridyl | 4-methoxyphenyl |
| (I-56) | ethyl(S) | CH | CH$_2$CH$_2$NHPh | 4-methoxyphenyl |
| (I-57) | ethyl(S) | CH | CH$_2$CH$_2$CO$_2$CH$_2$CH$_3$ | 4-methoxyphenyl |
| (I-58) | ethyl(S) | CH | CH$_2$CH$_2$CH$_2$Ph | 4-methoxyphenyl |
| (I-59) | ethyl(S) | CH | CH$_2$CH$_2$—N-Phthalimide | 4-methoxyphenyl |
| (I-60) | ethyl(S) | CH | CH$_2$CH$_2$CH$_2$CO$_2$CH$_2$CH$_3$ | 4-methoxyphenyl |
| (I-61) | ethyl(S) | CH | CH$_2$CH$_2$OCH$_2$CH$_3$ | 4-methoxyphenyl |
| (I-62) | ethyl(S) | CH | CH$_2$CH(CH$_3$)$_2$ | 4-methoxyphenyl |
| (I-63) | ethyl(S) | CH | CH$_2$CO$_2$CH$_2$CH$_3$ | 4-methoxyphenyl |
| (I-64) | ethyl(S) | CH | CH$_2$C(O)(4-Pyrrolidinophenyl) | 4-methoxyphenyl |
| (I-65) | ethyl(S) | CH | CH$_2$CH$_2$OPh | 4-methoxyphenyl |
| (I-66) | ethyl(S) | CH | CH$_2$CH$_2$CH$_2$CH$_2$—N-Phthalimide | 4-methoxyphenyl |
| (I-67) | ethyl(S) | CH | CH$_2$CO$_2$tBu | 4-methoxyphenyl |
| (I-68) | ethyl(S) | CH | CH$_2$CH$_2$CH(CH$_3$)$_2$ | 4-methoxyphenyl |
| (I-69) | ethyl(S) | CH | CH$_2$C(O)NH$_2$ | 4-methoxyphenyl |

TABLE-continued

Representative Compounds

| | | | | |
|---|---|---|---|---|
| (I-70) | ethyl(S) | CH | CH$_2$-4-(SO$_2$CH$_3$)Ph | 4-methoxyphenyl |
| (I-71) | ethyl(S) | CH | CH$_2$CH$_2$-1-Pyrrole | 4-methoxyphenyl |
| (I-72) | ethyl(S) | CH | CH$_2$Ph | 4-methoxyphenyl |

| Cpd | Analytical data (MS/$^1$H NMR) |
|---|---|
| (I-1) | 0.92(t, 6H), 1.25–1.34(m, 4H), 1.53–1.72(m, 4H), 2.11(s, 6H), 2.31(s, 3H), 2.46(s, 3H), 3.51(t, 2H), 4.02(t, 2H), 4.37–4.42(m, 1H), 6.98(s, 2H) |
| (I-2) | 0.93(t, 6H), 1.21–1.38(m, 4H), 1.52–1.60(m, 2H), 1.64–1.75(m, 2H), 2.34 (s, 3H), 2.49(s, 3H), 3.41(t, 2H), 3.72–3.79(m, 1H), 3.92–4.12(m, 2H), 6.25 (s, 1H), 7.05–7.78(m, 3H) |
| (I-3) | 0.93(t, 6H), 1.26(d, 6H), 1.27–1.35(m, 4H), 1.52–1.61(m, 4H), 2.41(s, 3H), 2.94(hept, 1H), 3.40(t, 2H), 3.73–3.82(m, 1H), 3.89–4.11(m, 2H), 6.26 (s, 1H), 7.27–7.58(m, 3H) |
| (I-4) | 0.93(t, 6H), 1.25–1.38(m, 4H), 1.52–1.62(m, 4H), 2.40(s, 3H), 3.40(t, 2H), 3.72–3.78(m, 1H), 3.90–4.11(m, 2H), 6.26(s, 1H), 7.26–7.57(m, 3H) |
| (I-5) | LC/MS 471(M + H) |
| (I-6) | 0.93(t, 6H), 1.25–1.39(m, 4H), 1.51–1.62(m, 4H), 2.44(s, 3H), 3.38(t, 2H), 3.72–3.79(m, 1H), 3.83(s, 3H), 3.99(t, 2H), 6.25(s, 1H), 6.99–7.61(m, 4H); MS(CI) m/z 395.10(MH$^+$); HRMS(FAB) m/z 417.2277(100; MNa$^+$ [C$_{23}$H$_{30}$N$_4$O$_2$Na] = 417.2266). |
| (I-7) | 7.50(d, 1H), 7.38(d, 1H), 7.16(dd, 1H), 6.42(s, 1H), 4.28–4.39(m, 1H), 4.09(t, 2H), 3.81(t, 2H), 1.92(s, 6H), 1.88–2.01(m, 2H), 1.64–1.75(m, 2H), 1.21–1.35(m, 4H), 0.91(t, 6H). |
| (I-8) | 7.72(d, 2H), 7.38(d, 2H), 6.20(s, 1H), 3.92(t, 2H), 3.63–3.72(m, 1H), 3.32 (t, 2H), 2.38(s, 3H), 1.40–1.57(m, 4H), 1.17–1.32(m, 4H), 0.86(t, 6H). |
| (I-9) | LC/MS 425(M + H) |
| (I-10) | LC/MS 395(M + H) |
| (I-11) | LC/MS 425(M + H) |
| (I-12) | LC/MS 433(M + H) |
| (I-13) | LC/MS 395(M + H) |
| (I-14) | 6.86(d, 1H), 6.83(d, 4H), 6.26(s, 1H), 4.01(t, 2H) <3.69–3.80(m, 1H), 3.40 (t, 2H), 2.41(s, 3H), 1.47–1.67(m, 4H), 1.25–1.39(m, 4H), 0.83(t, 6H). |
| (I-15) | 7.10(d, 1H), 6.53–6.56(m, 2H), 6.22(s, 1H), 3.95–4.10(m, 2H), 3.70–3.82(m, 1H), 3.12–3.40(m, 6H), 2.40(s, 3H), 1.51–1.60(m, 4H), 1.23–1.38(m, 4H), 1.16(t, 6H), 0.895–0.960(m, 6H) |
| (I-16) | 0.92(t, 6H), 1.28–1.41(m, 4H), 1.46–1.59(m, 4H), 2.43(s, 3H), 3.37(t, 2H), 3.71–3.77(m, 1H), 3.98(t, 2H), 4.27(s, 4H). 6.25(s, 1H), 6.93–7.26 (m, 3H); MS(CI) m/z 423.20(MH$^+$). |
| (I-17) | 7.61(d, 1H), 7.49(d, 1H), 7.31(dd, 1H); 6.27(s, 1H), 4.06–4.13(dt, 1H), 3.89–3.97(dt, 1H), 3.71–3.78(m, 1H), 3.42(t, 2H), 2.41(s, 3H), 1.53–1.63 (m, 4H), 1.28–1.39(m, 4H), 0.91–0.97(m, 6H). |
| (I-18) | 7.39–7.45(m, 1H), 6.10–7.076(m, 3H), 6.31(s, 1H), 4.04(t, 2H), 3.78–3.87(m, 4H), 3.52(t, 2H), 2.54(s, 3H), 1.59–1.67(m, 4H), 1.21–1.42(m, 4H), 0.95(t, 6H) |
| (I-19) | 7.09–7.21(m, 3H), 6.23(s, 1H), 3.93–4.15(m, 2H), 3.71–3.77(m, 1H), 3.93(t, 2H), 2.39(s, 3H), 2.35(s, 3H), 1.49–1.65(m, 4H), 1.26–1.41(m, 4H), 0.90–0.96(m, 6H) |
| (I-20) | 6.99(dd, 1H), 7.00(d, 1H), 6.72(d, 1H), 6.07(s, 1H), 5.82(s, 2H), 3.81(t, 2H), 3.51–3.61(m, 1H), 3.20(t, 2H), 2.26(s, 3H), 1.33–1.50(m, 4H), 1.07–1.21(m, 4H), 0.75(t, 6H). |
| (I-21) | 7.35(s, 1H), 7.277–7.281(m, 2H), 6.27(s, 1H), 3.95–4.07(m, 2H), 3.63(pentet, 1H), 3.41(t, 2H), 2.41(s, 3H), 2.25(s, 3H), 1.59–1.66(m, 4H), 1.19–1.36(m, 4H), 0.87–0.97(m, 6H) |
| (I-22) | 7.35(s, 1H), 7.277–7.281(m, 2H), 6.27(s, 1H), 3.93–4.06(m, 2H), 3.51–3.61(m, 1H), 3.41(t, 2H), 2.41(s, 3H), 2.25(s, 3H), 1.59–1.70(m, 4H), 0.95(t, 3H), 0.92(t, 3H) |
| (I-23) | 7.35(s, 1H), 7.275–7.28(m 2H), 6.26(s, 1H), 3.91–4.1(m, 2H), 3.6–3.75(m, 1H), 3.41(t, 2H), 2.41(s, 3H), 2.24(s, 3H), 1.54–1.68(m, 4H), 1.30–1.42(m, 2H), 0.90–0.97(m, 6H) |
| (I-24) | 7.35(s, 1H), 7.278–7.282(m, 2H), 6.26(s, 1H), 3.92–4.10(m, 2H), 3.624(pentet, 1H), 3.41(t, 2H), 2.41(s, 3H), 2.25(s, 3H), 1.54–1.68(m, 4H), 1.20–1.38(m, 6H), 0.84–0.97(m, 6H) |
| (I-25) | 7.35(s, 1H), 7.28(s, 2H), 62.4(s, 1H), 3.92–4.10(m, 2H), 3.72(pentet, 1H), 3.40(t, 2H), 2.40(s, 3H), 2.24(s, 3H), 1.56–1.62(m, 4H), 1.26–1.38(m, 6H), 0.86–0.97(m, 6H) |
| (I-26) | 7.01(d, 2H), 6.42(t, 1H), 6.26(s, 1H), 4.00(t, 2h), 3.80(s, 6H), 3.69–3.80 (m, 1H), 3.38(t, 2H), 2.45(s, 3H), 1.46–1.66(m, 4H), 1.23–1.38(m, 4H), 0.92(t, 6H). |
| (I-27) | 6.79(d, 1H), 6.29(s, 1H), 3.97(t, 2H), 3.69–3.79(m, 1H), 3.37(t, 2H), 2.51 (s, 3H), 2.47(d, 3H), 1.51–1.75(m, 4H), 1.25–1.37(m, 4H), 0.83–0.94(m, 6H). |
| (I-28) | 7.72(d, 2H), 7.33–7.38(m, 2H), 7.06–7.14(m, 5H), 4.00(t, 2H), 3.70–3.80 (m, 1H), 3.39(t, 2H), 2.45(s, 3H), 1.47–1.65(m, 4H), 1.25–1.39(m, 4H), 0.93(t, 6H). |

TABLE-continued

Representative Compounds (I-29) 8.57(d, 1H), 7.95(dd, 1H) <6.86(d, 1H), 6.26(s, 1H), 4.00(t, 2H), 3.91(s, 3H), 3.70–3.79(m, 1H), 3.39(t, 2H), 2.43(s, 3H), 1.51–1.67(m, 4H), 1.25–1.38(m, 4H), 0.92(t, 6H).
(I-30) 0.92(t, 6H), 1.25–1.38(m, 4H), 1.51–1.62(m, 4H), 2.42(s, 3H), 3.12(s, 6H), 3.38(t, 2H), 3.71–3.77(m, 1H), 3.99(t, 2H), 6.24(s, 1H), 6.63–8.47(m, 3H); MS(CI) m/z 409.20(MH$^+$).
(I-31) 7.66(d, 2H), 7.01(d, 2H), 6.2(s, 1H), 4.18(dd, 1H), 3.84(s, 3H), 3.54–3.72(m, 5H), 3.38–3.44(m, 1H), 3.37(s, 3H), 2.45(s, 3H), 1.31–1.73(m, 2H), 1.00(t, 3H)
(I-32) 7.62(d, 2H), 7.01(d, 2H), 6.23(s, 1H), 4.23(dd, 1H), 3.84(s, 3H), 3.60–3.81(m, 5H), 3.31–3.40(m, 1H), 2.44(s, 3H), 1.5–1.72(m, 2H), 1.01(t, 3H)
(I-33) 7.94(d, 2H), 7.30(d, 2H), 6.29(s, 1H), 4.01(t, 2H), 3.76(s, 1H), 3.41(t, 2H), 3.28(s, 3H), 2.48(s, 3H), 1.96(t, 3H), 1.49–1.68(m, 4H), 1.25–1.37(m, 4H), 0.94(t, 6H)
(I-34) 7.64(d, 2H), 7.01(d, 2H), 6.2(s, 1H), 4.18(dd, 1H), 3.84(s, 3H), 3.56–3.74(m, 3H), 3.22–3.32(m, 1H), 2.55–2.65(m, 6H), 2.45(s, 3H), 1.52–1.73(m, 2H), 0.98–1.07(m, 9H)
(I-35) δ 8.16(d, 2H), 8.05(d, 2H), 6.28(s, 1H), 4.00 t, 2H), 3.93(s, 3H), 3.71–3.81 (m, 1H), 3.39(t, 2H), 2.47(s, 3H), 1.52–1.65(m, 4H), 1.28–1.39(m, 4H), 0.92(t, 6H).
(I-36) δ 8.60(d, 1H), 7.82(dd, 1H), 7.74(d, 1H), 6.29(s, 1H), 3.99(t, 2H), 3.73–3.78(m, 1H), 3.87(t, 2H), 2.48(s, 3H), 1.51–1.62(m, 4H), 1.25–1.38(m, 4H), 0.92(t, 6H).
(I-37) δ 8.08(s, 4H), 6.29(s, 1H), 4.00(t, 2H), 3.71–3.81(m, 1H), 3.97(t, 2H), 2.62 (s, 3H), 2.47(s, 3H), 1.52–1.62(m, 4H), 1.22–1.39(m, 4H), 0.93(t, 6H).
(I-38) δ 7.72(d, 2H), 7.60(d, 2H), 6.27(s, 1H), 4.00(t, 2H), 3.68–3.82(m, 1H), 3.48(s, 6H), 3.39(t, 3H), 2.45(s, 3H), 1.54–1.63(m, 4H), 1.24–1.38(m, 4H), 1.08(t, 3H), 0.93(t, 3H).

Example 4

CRF Receptor Binding Activity

The compounds of this invention may be evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 ml Eppendorf tubes using approximately 1×10$^6$ cells per tube stably transfected with human CRF receptors. Each tube receives about 0.1 ml of assay buffer (e.g., Dulbecco's phosphate buffered saline, 10 mM magnesium chloride, 20 μM bacitracin) with or without unlabeled sauvagine, urotensin I or CRF (final concentration, 1 μM) to determine nonspecific binding, 0.1 ml of [$^{125}$] tyrosine—ovine CRF (final concentration ~200 pM or approximately the K$_D$ as determined by Scatchard analysis) and 0.1 ml of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (*Anal. Biochem.* 107:220, 1990).

Example 5

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 μl of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 μl of ethanol/aqueous hydrochloric acid and pooled with the first fraction. The samples are lyophilized and then resuspended with 500 μl sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound having the following structure:

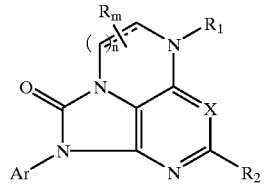

and stereoisomers and pharmaceutically acceptable salts thereof,
wherein:
n is 1;
m is 0, 1, 2 or 3;
X is N or CR';
R is an optional substituent which, at each occurrence, is independently $C_{1-6}$alkyl, $C_{3-6}$alkenyl, $C_{1-6}$alkylidenyl or $ArC_{1-6}$alkyl;
R' is hydrogen, halogen or $C_{1-6}$ alkyl;
$R_1$ is —$C(H)_{0,1}(R_3)(R_4)$;
$R_2$ is hydrogen or $C_{1-6}$alkyl;
$R_3$ is hydrogen, keto, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl, or $C_{1-6}$alkyloxy$C_{1-6}$alkyl, and
$R_4$ is hydrogen, $Ar^1$, $Ar^1C_{1-6}$alkyl, $OAr^1$, $C_{1-8}$alkyl, $C_{1-6}$alkyloxy, $C_{3-6}$cycloalkyl, mono- or di($C_{3-6}$cycloalkyl)methyl, $C_{3-6}$alkenyl, $C_{3-6}$alkynyl, $C_{1-6}$alkyloxy$C_{1-6}$alkyl, $C_{1-6}$alkoxyAr$^1$, hydroxy$C_{1-6}$alkyl, thienyl$C_{1-6}$alkyl, furanyl$C_{1-6}$alkyl, $C_{1-6}$alkylthio$C_{1-6}$alkyl, morpholinyl, mono- or di($C_{1-6}$alkyl)amino$C_{1-6}$alkyl, amino, ($C_{1-6}$alkyl)amino, di($C_{1-6}$alkyl)amino, ($C_{1-6}$alkylAr$^1$)amino, ($C_{1-6}$alkyl)(Ar$^1$)amino, $C_{1-6}$alkylcarbonyl$C_{1-6}$alkyl, $C_{1-6}$alkylcarbonyloxy$C_{1-6}$alkyl, sulfonyl($C_{1-8}$alkyl), $C(=O)C_{1-6}$alkyl, $C_{1-8}$alkyl substituted with phthalimide, $Ar^1$, $OAr^1$, $NHAr^1$, $C(=O)Ar^1$, $C(=O)NHAr^1$ or —$C(=O)NH_2$, or a radical of the formula —($C_{1-6}$alkanediyl)-Y—(CO)$_{0,1}$—$Ar^1$ where Y is O, NH or a direct bond, or
$R_3$ and $R_4$ taken together with the carbon atom to which they are attached form a $C_{3-8}$cycloalkyl, a $C_{5-8}$cycloalkenyl, a $C_{3-12}$heterocycle, phenyl, naphthyl, or a $C_{5-8}$cycloalkyl fused to $Ar^1$, each of which being optionally substituted with one or more substituents independently selected from $C_{1-6}$alkyl;
Ar is phenyl, naphthyl or an aromatic $C_{3-12}$heterocycle, each being optionally substituted with 1, 2 or 3 substituents independently selected from halo, $C_{1-6}$alkyl, trifluoromethyl, O(trifluoromethyl), hydroxy, cyano, $C_{1-6}$alkyloxy, phenyoxy, benzoxy, $C_{1-6}$alkylthio, nitro, amino, mono- or di($C_{1-6}$alkyl)amino, ($C_{1-6}$alkyl) ($C_{1-6}$alkanoyl)amino, or piperidinyl, or wherein two substituents taken together are a $C_{1-6}$alkylidinyl or a $C_6$alkylidenyl having one, two or three carbon atoms replaced with a heteroatom individually selected from oxygen, nitrogen or and sulfur; and
$Ar^1$ is phenyl, naphthyl or an aromatic $C_{3-12}$heterocycle, each of which being optionally substituted with 1, 2 or 3 substituents independently selected from halo, $C_{1-6}$alkyl, $C_{1-6}$alkyloxy, di($C_{1-6}$alkyl)amino, di($C_{1-6}$alkyl)amino$C_{1-6}$alkyl, trifluoromethyl, sulfonyl($C_{1-6}$alkyl) and $C_{1-6}$alkyl substituted with morpholinyl.

2. The compound of claim 1 having the structure

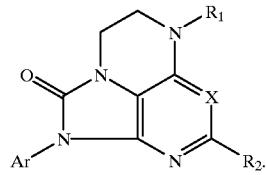

3. The compound of claim 1 having the structure

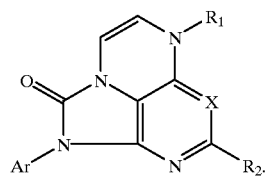

4. The compound of claim 1 wherein m is 0.
5. The compound of claim 4 having the structure:

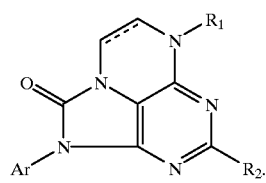

6. The compound of claim 4 having the structure:

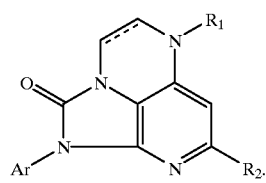

7. The compound of claim 1 wherein m is 1.
8. The compound of claim 7 having the structure:

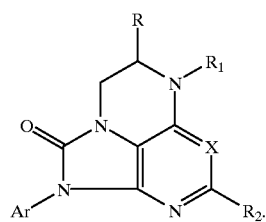

9. The compound of claim 7 having the structure:

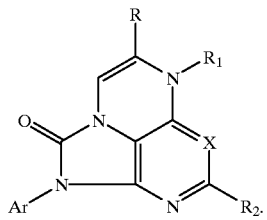

10. The compound of claim 1 wherein X is CR' and R' is hydrogen.
11. The compound of claim 1 wherein X is N.
12. The compound of claim 1 wherein R is $C_{1-6}$alkyl.
13. The compound of claim 1 wherein R is methyl or ethyl.
14. The compound of claim 1 wherein R is ethyl.
15. The compound of claim 1 wherein Ar is 2,4,6-trimethylphenyl, 2-chloro-4-methylphenyl, 2-chloro-4-methoxyphenyl, 2-bromo-4-methylphenyl, 2-methyl-4-chlorophenyl, 2-methyl-4-bromophenyl, 2-bromo-4-isopropylphenyl, 2,4-dichlorophenyl, 2,6-dimethyl-4-bromophenyl, 4-chlorophenyl, 2,4-dimethoxyphenyl, 2,4-dimethylphenyl, 2-methoxyphenyl, 3-methoxyphenyl, 4-methoxyphenyl, 2-methyl-4-methoxyphenyl, 3,4-dimethoxyphenyl, 3,5-dimethoxyphenyl, 4-trifluoromethylphenyl, 2,4,6-trifluorophenyl, 2-methyl-4-N(ethyl)$_2$phenyl, 2-bromo-4-(OCF$_3$)phenyl, 4-dimethylamino-2-methylpyrdin-3-yl, 4-dimethylamino-6-methylpyridin-3-yl, 4-dimethylamino-pyridin-3-yl, 4-N(CH$_3$)(Ac)phenyl, 5-methylisoxazol-3-yl, 3,4-methylenedioxyphenyl or 3,4-ethylenedioxyphenyl.
16. The compound of claim 1 wherein Ar is 2,4,6-trimethylphenyl, 2-methyl-4-chlorophenyl, 2-chloro-4-mnethylphenyl, 2,4-dichlorophenyl, 2,6-dimethyl-4-bromophenyl, 2-bromo-4-methylphenyl, 4-methoxyphenyl or 4-chlorophenyl.
17. The compound of claim 1 wherein $R_1$ is methyl, ethyl, n-propyl, iso-propyl, n-butyl, iso-butyl, n-pentyl, iso-pentyl, neo-pentyl, —CH(ethyl)$_2$, —CH(n-propyl)$_2$, —CH(n-butyl)$_2$, —CH$_2$CH$_2$OCH$_3$, —CH(methyl)(CH$_2$OCH$_3$), —CH(ethyl)(CH$_2$OCH$_3$), —CH(n-propyl)(CH$_2$OCH$_3$), —CH(n-butyl)(CH$_2$OCH$_3$), —CH(tert-butyl)(CH$_2$OCH$_3$), —CH(CH$_2$OCH$_3$)$_2$, —CH(benzyl)(CH$_2$OCH$_3$), —CH(4-chlorobenzyl)(CH$_2$OCH$_3$), —CH(CH$_2$OCH$_3$)(CH$_2$CH$_2$SCH$_3$), —CH(ethyl)(CH$_2$Obenzyl), —CH(methyl)(ethyl), —CH(methyl)(n-propyl), —CH(methyl)(n-butyl), —CH(methyl)(n-pentyl), —CH(methyl)(CH$_2$CH$_2$CH$_2$CH(CH$_3$)$_2$), —CH(ethyl) (n-propyl), —CH(ethyl)(n-butyl), —CH(ethyl)(n-pentyl), —CH(n-propyl)(n-butyl), —CH(n-propyl)(n-pentyl), cyclopropyl, cyclobutyl, cyclohexyl, 2-methylcyclohexyl, 3-methylcyclohexyl, 1,2,3,4-tetrahydronaphthyl (1 and 2), benzyl, 2-chlorobenzyl, —CH(methyl)(benzyl), —CH(ethyl)(benzyl), —CH(n-propyl)(benzyl), —CH(n-butyl)(benzyl), —CH$_2$(cyclopropyl), —CH$_2$(cyclobutyl), —CH$_2$CH(methyl)CH$_2$CH$_3$, —CH$_2$CH(ethyl)CH$_2$CH$_3$, —CH$_2$C(methyl)$_3$, —CH$_2$C≡CH, —CH$_2$C(=O)ethyl, —C(=O)cyclopropyl, —C(=O)NHbenzyl, —C(=O)methyl, —C(=O)benzyl, —C(=O)phenyl, —C(=O)ethyl, —C(=O)CH$_2$C(=O)Oethyl, —C(=O)CH(phenyl)ethyl, C(=O)pyridyl, —C(=O)(4-N,N-dimethylamino)phenyl, —C(=O)CH$_2$Omethyl, —C(=O)CH(ethyl)$_2$, —C(=O)n-butyl, —C(=O)CH$_2$CH$_2$(methyl)$_2$, —C(=O)n-propyl, —C(=O)CH$_2$CH$_2$phenyl, —CH$_2$pyridyl, —CH$_2$CH$_2$NHphenyl, —CH$_2$CH$_2$C(=O)Oethyl, —CH$_2$CH$_2$CH$_2$phenyl, —CH$_2$CH$_2$-N-phthalimide, —CH$_2$CH$_2$CH$_2$C(=O)Oethyl, —CH$_2$CH$_2$Oethyl, —CH$_2$CH(methyl)$_2$, —CH$_2$C(=O)pyrrolidinophenyl, —CH$_2$CH$_2$Ophenyl, —CH$_2$CH$_2$CH$_2$CH$_2$-N-phthalimide, —CH$_2$CH$_2$CH(methyl)$_2$, —CH$_2$C(=O)NH$_2$, —CH$_2$-4-(SO$_2$CH$_3$)phenyl, and —CH$_2$CH$_2$pyrrolyl.
18. The compound of claim 1 wherein $R_1$ is —CH(ethyl)$_2$, —CH(n-propyl)$_2$, —CH(ethyl)(n-butyl) or —CH(ethyl)(n-pentyl).

* * * * *

UNITED STATES PATENT AND TRADEMARK OFFICE
CERTIFICATE OF CORRECTION

PATENT NO.    : 6,348,466 B1
DATED         : February 19, 2002
INVENTOR(S)   : Mustapha Haddach et al.

It is certified that error appears in the above-identified patent and that said Letters Patent is hereby corrected as shown below:

Title page,
Item [57], ABSTRACT,
"Compounds are disclosed which have utility in the treatment of a variety of disorders, including the treatment of disorders manifesting hypersecretion of CRF in a warm-blooded animals, including stroke. The compounds of this invention have the following structures:

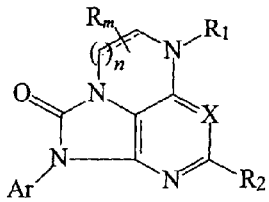

wherein $n$, $m$, R, $R_1$, $R_2$, X and Ar are as defined herein, including stereoisomes and pharmaceutically acceptable salts thereof." should be corrected to read -- Compounds are disclosed which have utility in the treatment of a variety of disorders, including the treatment of disorders manifesting hypersecretion of CRF in a warm-blooded animals, including stroke. The compounds of this invention have the following structures:

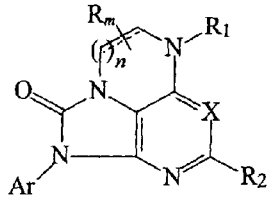

wherein $n$, $m$, R, $R_1$, $R_2$, X and Ar are as defined herein, including stereoisomes and pharmaceutically acceptable salts thereof. --

Column 26,
Line 3, "oxygen, nitrogen or and sulfur" should be corrected to read
-- oxygen, nitrogen, or sulfur --.

UNITED STATES PATENT AND TRADEMARK OFFICE
CERTIFICATE OF CORRECTION

PATENT NO. : 6,348,466 B1
DATED : February 19, 2002
INVENTOR(S) : Mustapha Haddach et al.

It is certified that error appears in the above-identified patent and that said Letters Patent is hereby corrected as shown below:

Column 27,
Lines 35 and 36, "2-chloro-4-mnethylphenyl" should be corrected to read
-- 2-chloro-4-methylphenyl --.

Signed and Sealed this

Twenty-sixth Day of November, 2002

Attest:

Attesting Officer

JAMES E. ROGAN
Director of the United States Patent and Trademark Office